(12) United States Patent
Foran et al.

(10) Patent No.: US 7,027,633 B2
(45) Date of Patent: Apr. 11, 2006

(54) COLLABORATIVE DIAGNOSTIC SYSTEMS

(76) Inventors: David J. Foran, 114 Short Hills Ave., Short Hills, NJ (US) 07078; Dorin Cominciu, 126 Forest Glen Dr., Highland Park, NJ (US) 08904; Peter Meer, 16 Timothy La., East Brunswick, NJ (US) 08816

( * ) Notice: Subject to any disclaimer, the term of this patent is extended or adjusted under 35 U.S.C. 154(b) by 626 days.

(21) Appl. No.: 09/998,359

(22) Filed: Nov. 29, 2001

(65) Prior Publication Data

US 2002/0106119 A1 Aug. 8, 2002

Related U.S. Application Data

(60) Provisional application No. 60/250,239, filed on Nov. 30, 2000.

(51) Int. Cl.
*G06K 9/00* (2006.01)

(52) U.S. Cl. ........................ 382/133; 128/920; 600/300

(58) Field of Classification Search ................ 382/128, 382/129, 130, 131, 132, 133, 134, 575; 435/6; 600/427, 300, 411; 128/906, 920; 378/43; 250/309, 311, 201.3, 461.2
See application file for complete search history.

(56) References Cited

U.S. PATENT DOCUMENTS

| | | | |
|---|---|---|---|
| 4,513,438 A | | 4/1985 | Graham et al. |
| 4,705,756 A * | 11/1987 | Spillert et al. ................ 436/64 |
| 5,016,283 A * | 5/1991 | Bacus et al. ................ 382/129 |
| 5,733,739 A * | 3/1998 | Zakim et al. ................ 435/29 |
| 5,793,969 A * | 8/1998 | Kamentsky et al. ........ 709/213 |
| 5,930,461 A | | 7/1999 | Bernstein et al. |
| 5,991,028 A * | 11/1999 | Cabib et al. ................ 356/456 |
| 6,078,681 A * | 6/2000 | Silver ........................ 382/133 |
| 6,103,466 A * | 8/2000 | Grobet et al. ................ 435/6 |
| 6,103,518 A | | 8/2000 | Leighton |
| 6,148,096 A | | 11/2000 | Pressman et al. |
| 6,226,392 B1 | | 5/2001 | Bacus et al. |
| 6,658,287 B1 * | 12/2003 | Litt et al. ................ 600/544 |
| 6,692,916 B1 * | 2/2004 | Bevilacqua et al. .......... 435/6 |

FOREIGN PATENT DOCUMENTS

WO  WO 93/14600  7/1993

(Continued)

OTHER PUBLICATIONS

Cabral, J.E. Jr. & Kim, Y. Multimedia Systems for Telemedicine and Their Communications Requirements. *IEEE Communications Magazine* 34, 20-27 (Jul. 1, 1996).

(Continued)

*Primary Examiner*—Kanjibhai Patel
*Assistant Examiner*—Abolfazl Tabatabai
(74) *Attorney, Agent, or Firm*—Fish & Neave IP Group, Ropes & Gray, LLP

(57) ABSTRACT

The systems described herein include tools for computer-assisted evaluation of objective characteristics of pathologies. A diagnostic system arranged according to the teachings herein provides computer support for those tasks well suited to objective analysis, along with human decision making where substantial discretion is involved. Collaborative diagnosis may be provided through shared access to data and shared control over a diagnostic tool, such as a telemicroscope, and messaging service for clinicians who may be at remote locations. These aspects of the system, when working in cooperation with one another, may achieve improved diagnostic accuracy or early detection for pathologies such as lymphoma.

24 Claims, 6 Drawing Sheets

FOREIGN PATENT DOCUMENTS

| WO | WO 96/07161 | 3/1996 |
|----|-------------|--------|
| WO | WO 99/30264 | 6/1999 |

OTHER PUBLICATIONS

Groshong, B.R. Estimating Simple Closed Contours in Images. *Proc. Ann. Symposium Comp. Based Med. Systems* 5, 35-43 (Jun. 14, 1992).

Garcia-Conde, J. and Cabanillas, F., "Mantle Cell Lymphoma: A Lymphoproliferative Disorder Associate with Aberrant Function of the Cell Cycle," Leukemia, vol. 10: (S2), pp.:S78-S83 (1996).

Vadlamudi, G., et al., "Leukemic Phase of Mantle Cell Lymphoma Two Case Reports and Review of the Literature", Arch. Pathol. Lab. Med., vol. 120, pp. 35-40 (1996).

Yatabe, Y, et al., "Clinicopathologic Study of PRAD1/Cyclin D1 Overexpressing Lymphoma with Special Reference to Mantle Cell Lymphoma", Amer. J. Surg. Pathol., vol. 20:(9), pp. 1110-1122 (1996).

Zink, S., and Jaffe, C. C., "Medical Imaging Databases, A National Institutes of Health Workshop," Investigative Radiol., vol. 28:(4), pp. 366-372 (1993).

Chan, J. K. C., et al., "A Revised European-American Classification of Lymphoid Neoplasms Proposed by the International Lymphoma Study Group," Amer. J. Clin. Pathol., vol. 103:(5), pp. 543-560 (1995).

Rozman, C., and Montserrat, E., "Chronic Lymphocytic Leukemia", N.E.J.M., vol. 333:(16), pp. 1052-1057 (1995).

Kilo, M. N., and Dorfman, D. M., "The Utility of Flow Cytometric Immunophenotypic Analysis in the Distinction of Small Lymphocytic Lymphoma/Chronic Lymphocytic Leukemia from Mantle Cell Lymphoma," Amer. J. Clin. Pathol., vol. 105, pp. 451-457 (1996).

Geisler, C. H., et al., "Prognostic Importance of Flow Cytomeric Immunophenotyping of 540 Consecutive Patients with B-Cell Chronic Lymphocytic Leukemia," Blood, vol. 78:(7), pp. 1795-1802 (1991).

Genesereth M., and Nilson, N., Logical Foundations of Artificial Intelligence, Palo Alto, CA: Morgan Kaufman,, pp. 19-45 (1988).

Bennett, J.M., et al., "Proposals for the Classification of the Acute Leukaemias", Br. J. Haematol., vol. 33, pp. 451-458 (1976).

Head, D. R., et al., "Reproducibility of the French-American-British Classification of Acute Leukemia: The Southwest Oncology Group Experience," Amer. J. Hematol., vol. 18, pp. 47-57 (1985).

Harms, H., et al., "Segmentation of Stained Blood Cell Images Measured at High Scanning Density with High Magnification and High Numerical Aperture Optics," Cytometry, vol. 7, pp. 522-531 (1986).

Baumann, I., et al., "Image Analysis Detects Lineage-Specific Morphologic Markers in Leukemic Blast Cells," Amer. J. Clin. Pathol., vol. 105:(1), pp. 23-30 (1995).

Comaniciu, D. and Meer, P., "Distribution Free Decomposition of Multivariate Data," Pattern Anal. Applicat., vol. 2, pp. 22-30 (1999).

Kendall, D.G., "A Survey of the Statistical Theory of Shape," Statistical Science, vol. 4(2), pp. 87-120 (1989).

Hu, M. K., et al., "Visual Pattern Recognition by Moment Invariants," IRE Trans. Inform. Theory Inform. Technol., vol. 8, pp. 179-187 (1962).

Dryden, I.L., and Mardia, K.V., Statistical Shape Analysis, West Sussex, U.K.: Wiley, pp. 251-278 (1998).

Khotanzad, A., and Hong, Y.H., "Invariant Image Recognition by Zernike Moments," IEEE Trans. Pattern Anal. Machine Intell., vol. 12(5), pp. 489-497 (1990).

Kkhotanzad, A., and Hong, Y. H., "Rotation Invariant Image Recognition Using Features Selected Via a Systematic Method", Pattern Recognit., vol. 23:10, pp. 1089-1101 (1990).

Kauppinen, H., et al., "An Experimental Comparison of Autoregressive and Fourier-Based Descriptors in 2D Shape Classification," IEEE Trans. Pattern Anal. Machine Intell., vol. 17(2), pp. 201-207 (1995).

Kuhl, F., P and Giardina, C.R., "Elliptic Fourier Features of a Closed Contour," Computer Graph. Image Process., vol. 18, pp. 236-258 (1982).

Mao, J. and Jain, A.K., "Texture Classification Segmentation Using Multiresolution Simultaneous Autoregressive Models," Pattern Recognit., vol. 25(2), pp. 173-188 (1992).

Grimes, G.J., "Remote Microscopy for Hi-Res Real-Time interactive pathology," Advanced Imaging., vol. 12:7, pp. 12-16 (1998).

* cited by examiner

COLLABORATIVE DIAGNOSTIC SYSTEMS

CROSS-REFERENCE TO RELATED APPLICATIONS

This application claims the benefit of, and incorporates by reference, the entire disclosure of U.S. Provisional Patent Application No. 60/250,239 filed on Nov. 30, 2000.

GOVERNMENT INTEREST

The United States Government may have rights in this invention pursuant to National Science Foundation grants IRI-9530546 and IRI-9618854.

BACKGROUND OF THE INVENTION

Differentiation among malignant lymphomas and leukemias affects how aggressively patients are treated, which medications are appropriate, and what levels of risk are justified. As more differentiated treatments become available, it has become increasingly important to distinguish among subclasses of blood pathologies. Nonetheless, discriminating among known pathologies may be difficult. As an example, mantle cell lymphoma ("MCL") is often misdiagnosed as chronic lymphocytic leukemia ("CLL") or as follicular center cell lymphoma ("FCC").

The classical morphological description of MCL is a monotonous proliferation of small to medium sized lymphoid cells with scant cytoplasm, variably irregular and indented nuclei, dispersed chromatin, inconspicuous nucleoli and scant cytoplasm. The immunophenotype is CD5 positive B cells which are FMC7 antigen positive with moderately bright surface membrane immunoglobin light chain expression, CD2d negative and usually CD10 negative. The lack of CD23 expression differentiates this entity from typical CLL, however confusion between these two can arise when CLL loses CD23 during disease progression.

The classical morphological description of typical CLL cells is small lymphocytes containing round nuclei with coarsely condensed chromatin and scant cytoplasm. The immunophenotype for CLL is CD5 positive antigen expression on B cells with CD23 antigen positivity, low density surface membrane immunoglobulin restricted light chain positivity and CD10 negative. This immunophenotype is considered the diagnostic gold standard for CLL. However, atypical CLL may be associated with deviations in immunophenotype that lead to a misdiagnosis as mantle cell lymphoma.

The classical morphological description of FCC cells is small to medium sized lymphoid cells with markedly angulated and cleaved nuclei, coarse chromatin, inconspicuous nucleoli and scant cytoplasm. The classic immunophenotype consists of CD5 negative B cells with positive CD10 expression and moderately bright expression of surface membrane immunoglobulin light chain expression.

The subtle visual differences exhibited by these pathologies give rise to a significant number of false negatives during routine screening. When suspicious cells are detected, subsequent evaluation of specimens by even experienced pathologists may be inconclusive. In these cases a diagnosis is not rendered until the specimen has been immunophenotyped. Additional testing is expensive, time-consuming, and often requires fresh tissue which may not be readily available. Because it would be impractical to immunophenotype every specimen, it would be useful to reduce the frequency of false negatives and improve discrimination among commonly confused lymphoproliferative disorders without resort to immunophenotyping. The timely diagnosis of, for example, MCL is of extreme importance since it has a more aggressive clinical course.

There remains a need for diagnostic tools to assist in discriminating among pathologies with similar characteristics and different courses of treatment.

SUMMARY OF THE INVENTION

The systems described herein include tools for computer-assisted evaluation of objective characteristics of pathologies. A diagnostic system arranged according to the teachings herein provides computer support for those tasks well suited to objective analysis, along with human decision making where substantial discretion is involved. Collaborative diagnosis may be provided through shared access to data and shared control over a diagnostic tool, such as a telemicroscope, and messaging service for clinicians who may be at remote locations. These aspects of the system, when working in cooperation with one another, may achieve improved diagnostic accuracy or early detection for pathologies such as lymphoma.

A system described herein may include a microscope that provides an image of a biological specimen in digital form, the microscope responsive to a control signal to change a parameter used to obtain the image of the biological specimen, the parameter including at least one of an objective lens, a focus, a light level, and a specimen position. The system may include a database that includes one or more pathology profiles associated with one or more pathologies, the one or more pathology profiles derived from images of one or more other biological specimens having one or more pathologies. The system may further include a decision support system that processes the image from the microscope to obtain an image profile, the image profile including descriptive data of the image, the decision support system comparing the image profile to the one or more pathology profiles in the database to identify one or more of the one or more pathologies that are candidates for a pathology associated with the biological specimen; and the system may include a client interface through which one or more remote users receive the image of the biological specimen and provide input to the system including at least one of generating the control signal to the microscope, communicating with other ones of the one or more remote users, and controlling operation of the decision support system. The one or more pathologies may include hematological disorders.

In the system, the microscope may employ an auto-focusing algorithm that retains a history of one or more previous auto-focus settings. The system may further include an archival system which provides unsupervised image feature extraction and automated management of images of additional biological specimens for addition to the database. The decision support system may be trained using a ground truth database of images having independently confirmed pathologies. The pathologies may be independently confirmed using at least one of immunophenotyping, molecular studies, or gene expression. The decision support system may compare the image profile to one of the one or more pathology profiles by quantitatively comparing a derived measure of shape, texture, and area for the image profile to a derived measure of shape, texture, and area for the one of the one or more pathology profiles. The derived measure of shape may be a plurality of elliptical Fourier coefficients for an outline of a shape of one or more components of the biological specimen. The derived measure of texture may be calculated using a multiscale simultaneous autoregressive model.

A method as described herein may include providing a database that includes one or more pathology profiles associated with one or more cells having one or more pathologies, the pathology profile for each pathology including a shape measure derived from a shape of one or more cells associated with the pathology, a texture measure derived from a texture of the one or more cells associated with the pathology, and an area measure derived from an area of the one or more cells associated with the pathology; receiving an image of a cell in digital form; processing the received image to obtain a query vector that includes a shape measure of the cell in the received image, a texture measure of the cell in the received image, and an area of the cell in the received image; and comparing the query vector to the one or more pathology profiles in the database to obtain a quantitative measure of similarity between the cell in the received image and one of the one or more cells having one or more pathologies.

The method may further include suggesting a diagnosis for the cell in the received image based upon the quantitative measure of similarity. Comparing the query vector to the one or more pathology profiles may further include calculating, for each pathology profile in the database, a weighted sum of a difference between each of the shape measure, the texture measure, and the area for the pathology profile and the shape measure, the texture measure, and the area for the query vector. The one or more pathologies may include one or more hematological disorders. Processing the received image may further include: converting the image from a red-green-blue representation to a luminance-chrominance representation; locating a plurality of coordinates of an outer boundary of at least one of the cell or one or more constituent components of the cell; and characterizing the outer boundary with a plurality of elliptical Fourier coefficients. Processing the received image may further include selecting a plurality of overlapping windows within the received image and, for each one of the plurality of overlapping windows, calculating a texture at a plurality of resolutions. The method may further include applying a multiscale simultaneous autoregressive model.

In another aspect, a system as described herein includes: database means for providing a database that includes one or more pathology profiles associated with one or more cells having one or more pathologies, the pathology profile for each pathology including a shape measure derived from a shape of one or more cells associated with the pathology, a texture measure derived from a texture of the one or more cells associated with the pathology, and an area measure derived from an area of the one or more cells associated with the pathology; imaging means for receiving an image of a cell in digital form; processing means for processing the received image to obtain a query vector that includes a shape measure of the cell in the received image, a texture measure of the cell in the received image, and an area of the cell in the received image; and comparing means for comparing the query vector to the one or more pathology profiles in the database to obtain a quantitative measure of similarity between the cell in the received image and one of the one or more cells having one or more pathologies.

A computer program product as described herein may include: computer executable code for providing a database that includes one or more pathology profiles associated with one or more cells having one or more pathologies, the pathology profile for each pathology including a shape measure derived from a shape of one or more cells associated with the pathology, a texture measure derived from a texture of the one or more cells associated with the pathology, and an area measure derived from an area of the one or more cells associated with the pathology; computer executable code for receiving an image of a cell in digital form; computer executable code for processing the received image to obtain a query vector that includes a shape measure of the cell in the received image, a texture measure of the cell in the received image, and an area of the cell in the received image; and computer executable code for comparing the query vector to the one or more pathology profiles in the database to obtain a quantitative measure of similarity between the cell in the received image and one of the one or more cells having one or more pathologies.

In another aspect, a method as described herein may include: providing a database that includes one or more pathology profiles associated with one or more pathologies, the pathology profile for each pathology including a shape, a texture, and an area for one or more images of biological specimens that carry the pathology; providing a decision support system for comparing a new specimen to the one or more pathology profiles and identifying a pathology from the one or more pathology profiles associated with the new specimen; and providing a server that includes a client interface through which a user may submit the new specimen to the decision support system from a remote location in a network, the server providing a result from the decision support system to the user at the remote location.

The server may be further configured to share the result and the image among a plurality of users, and to forward electronic communications between two or more of the plurality of users. The electronic communications may include at least one of instant messaging, audio, text, or electronic mail. The method may further include providing a microscope that provides an image of a biological specimen in digital form, the microscope responsive to a control signal to change a parameter used to obtain the image of the biological specimen, the parameter including at least one of an objective lens, a focus, a light level, and a specimen position; and providing a user interface through which one or more of a plurality of users, connected to the client interface through a data network, receive the image of the biological specimen and generate the control signal to the microscope. One of the plurality of users may have a token that provides to the one of the plurality of users exclusive control over the control signal to the microscope. The decision support system may compare a measure of shape, a measure of texture, and an area of the new specimen to a measure to a measure of shape, a measure of texture, and an area of each of the one or more pathology profiles.

BRIEF DESCRIPTION OF DRAWINGS

The foregoing and other objects and advantages of the invention will be appreciated more fully from the following further description thereof, with reference to the accompanying drawings, wherein.

DETAILED DESCRIPTION OF CERTAIN EMBODIMENTS OF THE INVENTION

To provide an overall understanding of the invention, certain illustrative embodiments will now be described, including a system for collaborative, computer-aided discrimination among lymphoproliferative pathologies. However, it will be understood that the methods and systems described herein can be suitably adapted to any environment where discrimination among similar visual samples or detection of a pathology based upon visual features would benefit from a combination of computer-aided and collaborative human diagnosis. For example, the systems and methods are applicable to a wide range of biological specimen images, including medical diagnostic applications, such as radiology, and in particular to diagnosis involving analysis of cellular, or other microscopic, visual data. These and other applications of the systems described herein are intended to fall within the scope of the invention. More generally, the principles of the invention are generally applicable to any environment where shared access to, and control of, image data can be usefully combined with computer-assisted analysis.

Figure 1:
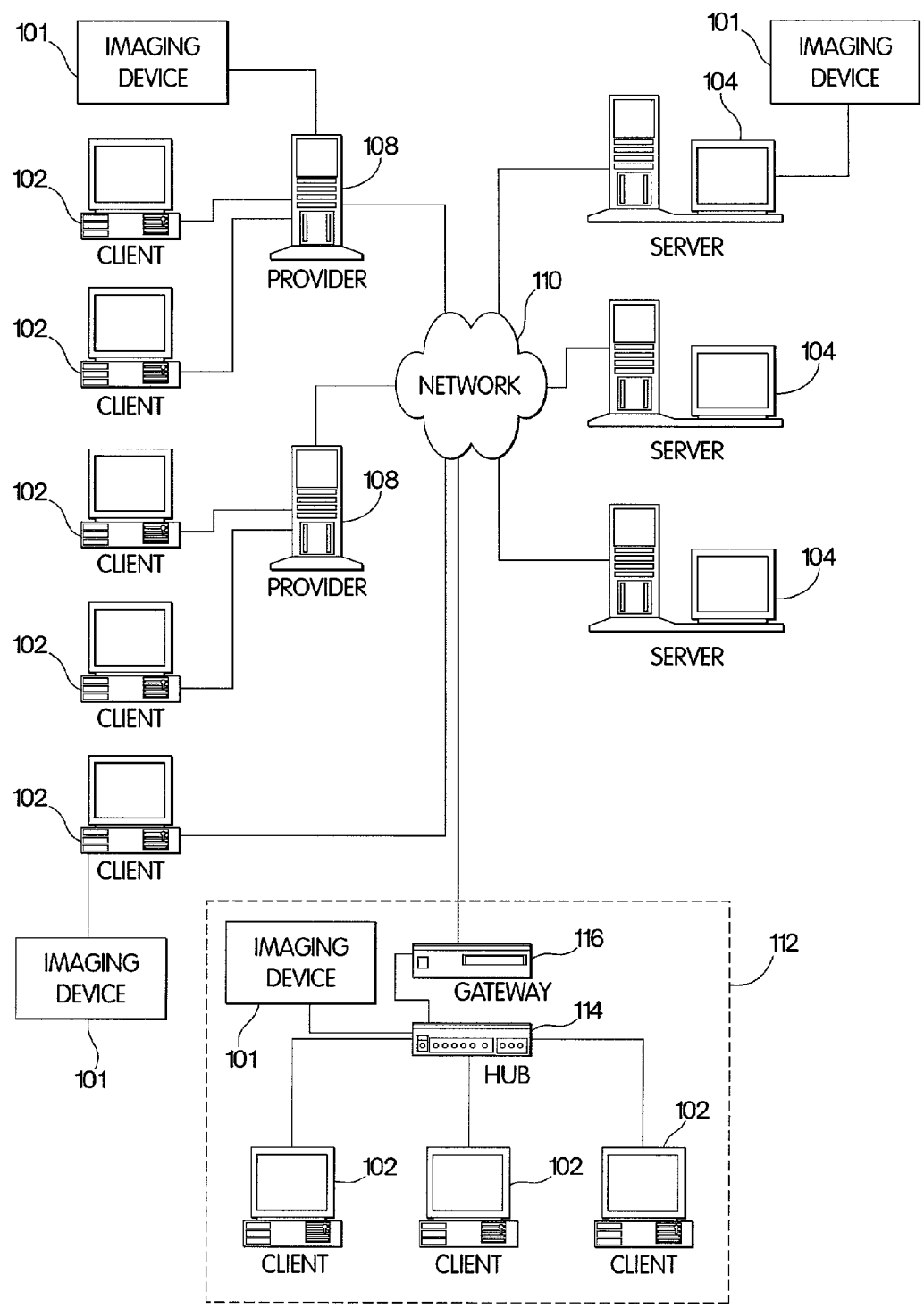
FIG. 1 shows a schematic diagram of the entities involved in an embodiment of a method and system disclosed herein.

FIG. 1 shows a schematic diagram of the entities involved in an embodiment of a method and system disclosed herein. In a system 100, one or more imaging devices 101, a plurality of clients 102, servers 104, and providers 108 are connected via an internetwork 110. It should be understood that any number of clients 102, servers 104, and providers 108 could participate in such a system 100. The system may further include one or more local area networks ("LAN") 112 interconnecting clients 102 through a hub 114 (in, for example, a peer network such as Ethernet) or a local area network server 114 (in, for example, a client-server network). The LAN 112 may be connected to the internetwork 110 through a gateway 116, which provides security to the LAN 112 and ensures operating compatibility between the LAN 112 and the internetwork 110. Any data network may be used as the internetwork 110 and the LAN 112.

In one embodiment, the internetwork 110 is the Internet, and the World Wide Web provides a system for interconnecting imaging devices 101, clients 102 and servers 104 through the Internet 110. The internetwork 110 may include a cable network, a wireless network, and any other networks for interconnecting clients, servers and other devices.

As depicted, one of the imaging devices 101 may be connected to one of the clients 102, one of the servers 104, the hub 114 of the LAN 112, or directly to one of the providers 108, and may include suitable hardware and software for connecting to the internetwork 110 through any of the above devices or systems. One of the imaging devices 101 that may be used in the systems herein is a high-resolution color video camera, such as an Olympus OLY-750 coupled to a Coreco, Occulus data acquisition board. This imaging device 101 may be used to gather images for the image database, as described in more detail below. Another one of the imaging devices 101 may be a robotic microscope, such as an Olympus AX70, allowing electronic control over a specimen stage, a light level, an objective lens, and a focus, as well as parameters of digitization such as rate and resolution. This imaging device 101 may be used to obtain a query image. More generally, the term 'imaging device' as used herein should be understood to include cameras, microscopes, or any other device for capturing and/or providing an image in electronic form, and should further be understood to include to include a mass storage device or other device for providing a previously captured electronic image.

An exemplary client 102 includes the conventional components of a client system, such as a processor, a memory (e.g. RAM), a bus which couples the processor and the memory, a mass storage device (e.g. a magnetic hard disk or an optical storage disk) coupled to the processor and the memory through an I/O controller, and a network interface coupled to the processor and the memory, such as modem, digital subscriber line ("DSL") card, cable modem, network interface card, wireless network card, or other interface device capable of wired, fiber optic, or wireless data communications. One example of such a client 102 is a personal computer equipped with an operating system such as Microsoft Windows 2000, Microsoft Windows NT, Unix, Linux, and Linux variants, along with software support for Internet communication protocols. The personal computer may also include a browser program, such as Microsoft Internet Explorer or Netscape Navigator, to provide a user interface for access to the Internet 110. Although the personal computer is a typical client 102, the client 102 may also be a workstation, mobile computer, Web phone, television settop box, interactive kiosk, personal digital assistant, or other device capable of communicating over the Internet 110. As used herein, the term "client" is intended to refer to any of the above-described clients 102, as well as proprietary network clients designed specifically for the systems described herein, and the term "browser" is intended to refer to any of the above browser programs or other software or firmware providing a user interface for navigating the Internet 110 and/or communicating with the medical image processing systems.

An exemplary server 104 includes a processor, a memory (e.g. RAM), a bus which couples the processor and the memory, a mass storage device (e.g. a magnetic or optical disk) coupled to the processor and the memory through an I/O controller, and a network interface coupled to the processor and the memory. Servers may be organized as layers of clusters in order to handle more client traffic, and may include separate servers for different functions such as a database server, a file server, an application server, and a Web presentation server. Such servers may further include one or more mass storage devices such as a disk farm or a redundant array of independent disk ("RAID") system for additional storage and data integrity. Read-only devices, such as compact disc drives and digital versatile disc drives, may also be connected to the servers. Suitable servers and mass storage devices are manufactured by, for example, Compaq, IBM, and Sun Microsystems. As used herein, the term "server" is intended to refer to any of the above-described servers 104.

Focusing now on the internetwork 110, one embodiment is the Internet. The structure of the Internet 110 is well known to those of ordinary skill in the art and includes a network backbone with networks branching from the backbone. These branches, in turn, have networks branching from them, and so on. The backbone and branches are connected by routers, bridges, switches, and other switching elements that operate to direct data through the internetwork 110. However, one may practice the present invention on a wide variety of communication networks. For example, the internetwork 110 can include interactive television networks, telephone networks, wireless data transmission systems, two-way cable systems, customized computer networks, interactive kiosk networks, or ad hoc packet relay networks.

One embodiment of the internetwork 110 includes Internet service providers 108 offering dial-in service, such as Microsoft Network, America OnLine, Prodigy and CompuServe. It will be appreciated that the Internet service providers 108 may also include any computer system which can provide Internet access to a client 102. Of course, the Internet service providers 108 are optional, and in some cases, the clients 102 may have direct access to the Internet 110 through a dedicated DSL service, ISDN leased lines, T1 lines, digital satellite service, cable modem service, or any other high-speed connection to a network point-of-presence. Any of these high-speed services may also be offered through one of the Internet service providers 108.

In its present deployment as the Internet, the internetwork 110 consists of a worldwide computer network that communicates using protocols such as the well-defined Transmission Control Protocol ("TCP") and Internet Protocol ("IP") to provide transport and network services. Computer systems that are directly connected to the Internet 110 each have a unique IP address. The IP address consists of four one-byte numbers (although a planned expansion to sixteen bytes is underway with IPv6). The four bytes of the IP address are commonly written out separated by periods such as "xxx.xxx.xxx.xxx". To simplify Internet addressing, the Domain Name System ("DNS") was created. The DNS allows users to access Internet resources with a simpler alphanumeric naming system. A DNS name consists of a series of alphanumeric names separated by periods. For example, the name "www.umdnj.edu" corresponds to a particular IP address. When a domain name is used, the computer accesses a DNS server to obtain the explicit four-byte IP address. It will be appreciated that other internetworks 110 may be used with the invention. For example, the internetwork 110 may be a wide-area network, a local area network, or corporate area network.

To further define the resources on the Internet 110, the Uniform Resource Locator system was created. A Uniform Resource Locator ("URL") is a descriptor that specifically defines a type of Internet resource along with its location. URLs have the following format:

resource-type://domain.address/path-name where resource-type defines the type of Internet resource. Web documents are identified by the resource type "http" which indicates that the hypertext transfer protocol should be used to access the document. Other common resource types include "ftp" (file transmission protocol), "mailto" (send electronic mail), "file" (local file), and "telnet." The domain.address defines the domain name address of the computer that the resource is located on. Finally, the path-name defines a directory path within the file system of the server that identifies the resource. As used herein, the term "IP address" is intended to refer to the four-byte Internet Protocol address (or the sixteen-byte IPv6 address), and the term "Web address" is intended to refer to a domain name address, along with any resource identifier and path name appropriate to identify a particular Web resource. The term "address," when used alone, is intended to refer to either a Web address or an IP address.

In an exemplary embodiment, a browser, executing on one of the clients 102, retrieves a Web document at an address from one of the servers 104 via the internetwork 110, and displays the Web document on a viewing device, e.g., a screen. A user can retrieve and view the Web document by entering, or selecting a link to, a URL in the browser. The browser then sends an http request to the server 104 that has the Web document associated with the URL. The server 104 responds to the http request by sending the requested Web document to the client 102. The Web document is an HTTP object that includes plain text (ASCII) conforming to the HyperText Markup Language ("HTML"). Other markup languages are known and may be used on appropriately enabled browsers and servers, including the Dynamic HyperText Markup Language ("DHTML"), the Extensible Markup Language ("XML"), the Extensible Hypertext Markup Language ("XHTML"), and the Standard Generalized Markup Language ("SGML").

Each Web document may contains hyperlinks to other Web documents. The browser displays the Web document on the screen for the user and the hyperlinks to other Web documents are emphasized in some fashion such that the user can identify and select each hyperlink. To enhance functionality, a server 104 may execute programs associated with Web documents using programming or scripting languages, such as Perl, C, C++, or Java. A server 104 may also use server-side scripting languages such as ColdFusion from Allaire, Inc., or PHP. These programs and languages perform "back-end" functions such as transaction processing, database management, content searching, and implementation of application logic for applications. A Web document may also include references to small client-side applications, or applets, that are transferred from the server 104 to the client 102 along with a Web document and executed locally by the client 102. Java is one popular example of a programming language used for applets. The text within a Web document may further include (non-displayed) scripts that are executable by an appropriately enabled browser, using a scripting language such as JavaScript or Visual Basic Script. Browsers may further be enhanced with a variety of helper applications to interpret various media including still image formats such as JPEG and GIF, document formats such as PS and PDF, motion picture formats such as AVI and MPEG, and sound formats such as MP3 and MIDI. These media formats, along with a growing variety of proprietary media formats, may be used to enrich a user's interactive and audio-visual experience as each Web document is presented through the browser. The term "page" as used herein is intended to refer to the Web document described above, as well as any of the above-described functional or multimedia content associated with the Web document.

Figure 2:
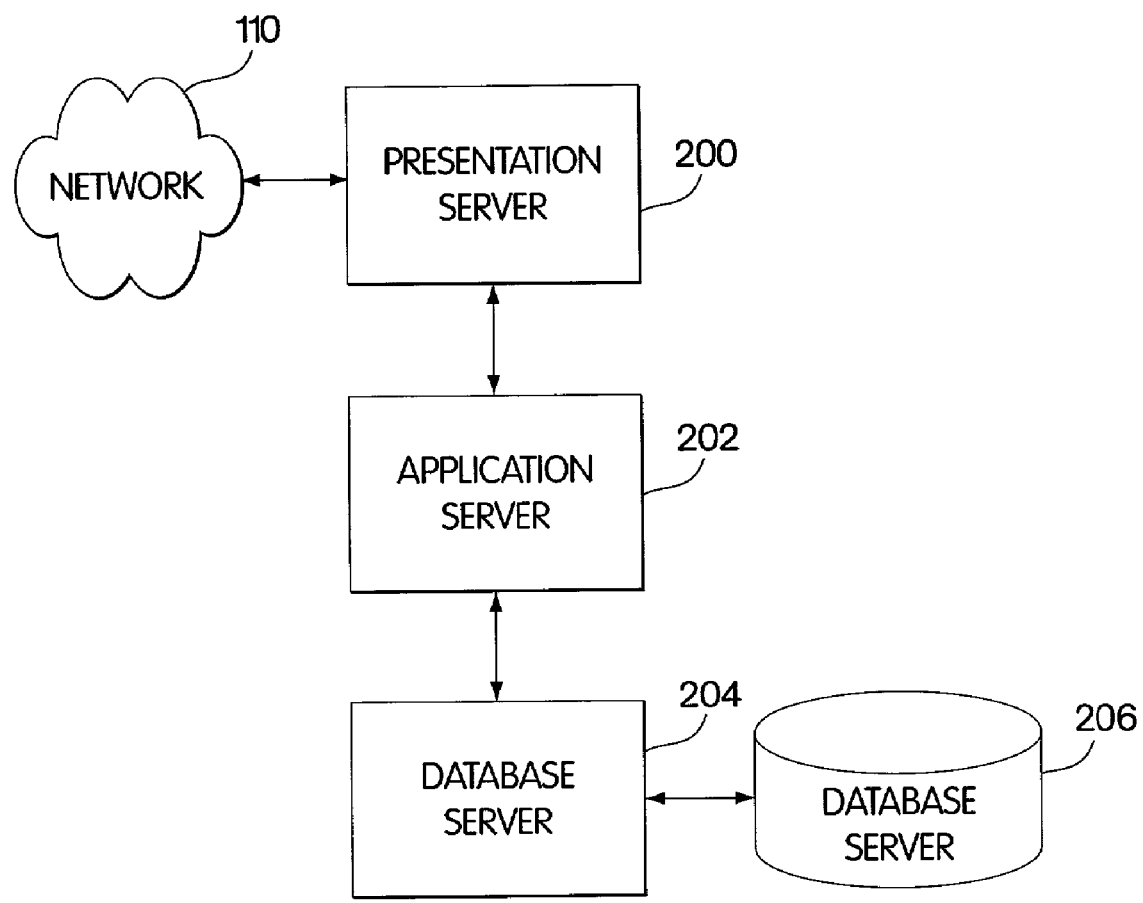
FIG. 2 shows a block diagram of a server that may be used with the systems described herein.

FIG. 2 shows a block diagram of a server that may be used with the systems described herein. In this embodiment, the server 104 includes a presentation server 200, an application server 202, and a database server 204. The application server 202 is connected to the presentation server 200. The database server 204 is also connected to the presentation server 200 and the application server 202, and is further connected to a database 206 embodied on a mass storage device. The presentation server 200 includes a connection to the internetwork 110. It will be appreciated that each of the servers may comprise more than one physical server, as required for capacity and redundancy, and it will be further appreciated that in some embodiments more than one of the above servers may be logical servers residing on the same physical device. One or more of the servers may be at a remote location, and may communicate with the presentation server 200 through a local area or wide area network. The term "host," as used herein, is intended to refer to any combination of servers described above that include a presentation server 200 for providing access to pages by the clients 102.

The term "site," as used herein, is intended to refer to a collection of pages sharing a common domain name address, or dynamically generated by a common host, or accessible through a common host (i.e., a particular page may be maintained on or generated by a remote server, but nonetheless be within a site).

The presentation server 200 provides an interface for one or more connections to the intenetwork 110, thus permitting more than one of the clients 102 (FIG. 1) to access the site at the same time. In one embodiment, the presentation server 200 comprises a plurality of enterprise servers, such as the ProLiant Cluster available from Compaq Computer Corp., or a cluster of E250's from Sun MicroSystems running Solaris 2.7. Other suitable servers are known in the art and are and may be adapted to use with the systems described herein, such as, for example, an iPlanet Enterprise Server 4.0 from the Sun/Netscape Alliance. The presentation server 200 may also use, for example, Microsoft's NET technology, or use a Microsoft Windows operating system, with a "front end" written in Microsoft Active Server Page ("ASP"), or some other programming language or server software capable of integrating ActiveX controls, forms, Visual Basic Scripts, JavaScript, Macromedia Flash Technology multimedia, e-mail, and other functional and multimedia aspects of a page. Typically, the front end includes all text, graphics, and interactive objects within a page, along with templates used for dynamic page creation. The presentation server 200 maintains one or more connections to the Internet 110. Where there is substantial network traffic, the connections are preferably provided by a tier one provider, i.e., one of the dozen or so national/international Internet backbones with cross-national links of T3 speeds or higher, such as MCI, UUNet, BBN Planet, and Digex.

A client 102 (FIG. 1) accessing an address hosted by the presentation server 200 will receive a page from the presentation server 200 containing text, forms, scripts, active objects, hyperlinks, etc., which may be collectively viewed using a browser. Each page may consist of static content, i.e., an HTML text file and associated objects (*.avi, *.jpg, *.gif, etc.) stored on the presentation server, and may include active content including applets, scripts, and objects such as check boxes, drop-down lists, and the like. A page may be dynamically created in response to a particular client 102 request, including appropriate queries to the database server 204 for particular types of data to be included in a responsive page. It will be appreciated that accessing a page is more complex in practice, and includes, for example, a DNS request from the client 102 to a DNS server, receipt of an IP address by the client 102, formation of a TCP connection with a port at the indicated IP address, transmission of a GET command to the presentation server 200, dynamic page generation (if required), transmission of an HTML object, fetching additional objects referenced by the HTML object, and so forth.

The application server 202 provides the "back-end" functionality of the Web site, and includes connections to the presentation server 200 and the database server 204. In one embodiment, the presentation server 200 comprises an enterprise server, such as one available from Compaq Computer Corp., running the Microsoft Windows NT operating system, or a cluster of E250's from Sun MicroSystems running Solaris 2.7. The back-end software may be implemented using pre-configured e-commerce software, such as that available from Pandesic, to provide back-end functionality including transaction processing, billing, data management, financial transactions, order fulfillment, and the like.

The e-commerce software running on the application server 202 may include a software interface to the database server 204, as well as a software interface to the front end provided by the presentation server 200. The application server 200 may also use a Sun/Netscape Alliance Server 4.0. A payment transaction server may also be included to process payments at a Web site using third party services such as Datacash or WorldPay, or may process payments directly using payment server and banking software, along with a communication link to a bank.

The database server 204 may be an enterprise server, such as one available from Compaq Computer Corp., running the Microsoft Windows NT operating system or a cluster of E250's from Sun MicroSystems running Solaris 2.7, along with software components for database management. Suitable databases are provided by, for example, Oracle, Sybase, and Informix. The database server 204 may also include one or more databases 206, typically embodied in a mass-storage device. The databases 206 may include, for example, user interfaces, search results, search query structures, lexicons, user information, and the templates used by the presentation server to dynamically generate pages. It will be appreciated that the databases 206 may also include structured or unstructured data, as well as storage space, for use by the presentation server 200 and the application server 202. In operation, the database management software running on the database server 204 receives properly formatted requests from the presentation server 200, or the application server 202. In response, the database management software reads data from, or writes data to, the databases 206, and generates responsive messages to the requesting server. The database server 204 may also include a File Transfer Protocol ("FTP") or a Secure Shell ("SSH") server for providing downloadable files.

While the three tier architecture described above is one conventional architecture that may be used with the systems described herein, it will be appreciated that other architectures for providing data and processing through a network are known and may be used in addition to, or in conjunction with, or in place of the described architecture. Any such system may be used, provided that it can support aspects of the image processing system described herein.

Figure 3:
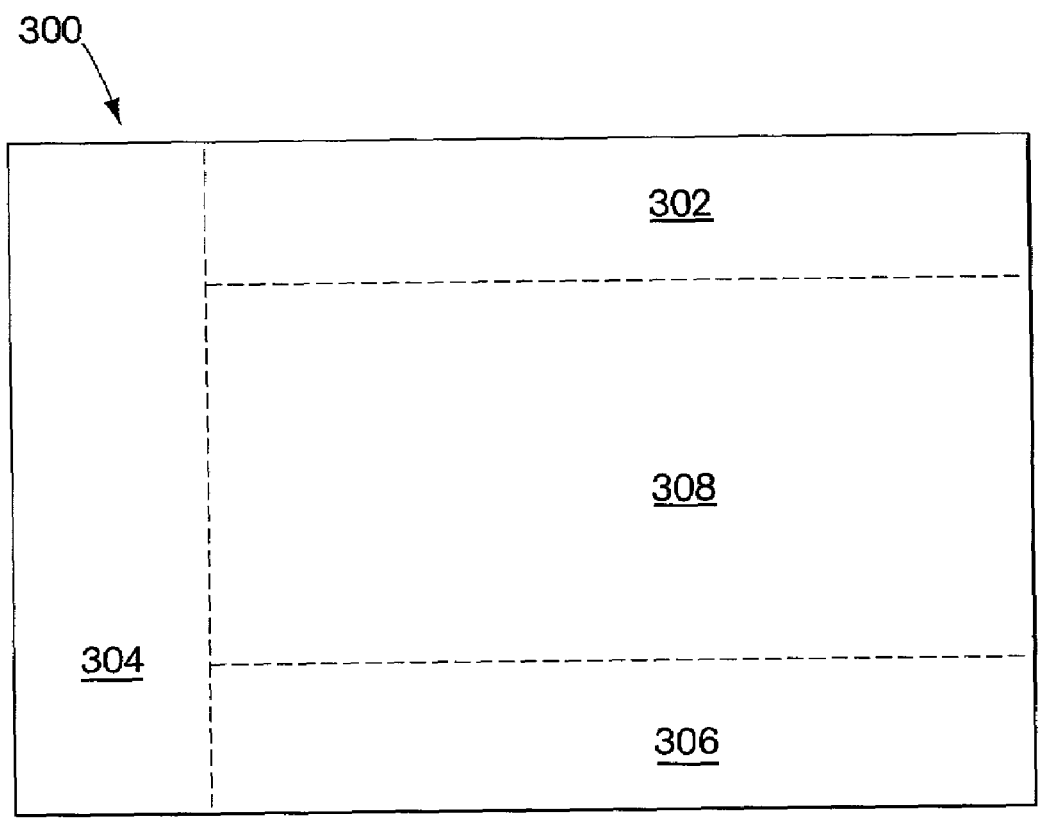
FIG. 3 shows a page that may be used as a user interface.

FIG. 3 shows a page that may be used as a user interface. The page 300 may include a header 302, a sidebar 304, a footer 306 and a main section 308, all of which may be displayed at a client 102 using a browser. The header 302 may include, for example, one or more banner advertisements and a title of the page. The sidebar 304 may include a menu of choices for a user at the client 102. The footer 306 may include another banner advertisement, and/or information concerning the site such as a "help" or "webmaster" contact, copyright information, disclaimers, a privacy statement, etc. The main section 308 may include content for viewing by the user. The main section 308 may also include, for example, tools for electronically mailing the page to an electronic mail ("e-mail") account, searching content at the site, and so forth. It will be appreciated that the description above is generic, and may be varied according to where a client 102 is within a Web site related to the page, as well as according to any available information about the client 102 (such as display size, media capabilities, etc.) or the user.

A Web site including the page 300 may use cookies to track users and user information. In particular, a client 102 accessing the site may be accessed to detect whether the client 102 has previously accessed the page or the site. If the client 102 has accessed the site, then some predetermined content may be presented to the client 102. If the client 102 does not include a cookie indicating that the client 102 has visited the site, then the client 102 may be directed to a registration page where information may be gathered to create a user profile. The client 102 may also be presented with a login page, so that a pre-existing user on a new client 102 may nonetheless bypass the registration page.

The site may provide options to the client 102. For example, the site may provide a search tool by which the client 102 may search for content within the site, or content external to the site but accessible through the internetwork 110. The site may include news items topical to the site. Banner ads may be provided in the page 300, and the ads may be personalized to a client 102 if a profile exists for that client 102. The banner ads may also track redirection. That is, when a client 102 selects a banner ad, the link and the banner ad may be captured and stored in a database. The site may provide a user profile update tool by which the client 102 may make alterations to a user profile.

It will be appreciated that the foregoing description has been generic. A user interface for a medical image processing system will now be described in more detail. The interface may be embodied in any software and/or hardware client operating on a client device, including a browser along with any suitable plug-ins, a Java applet, a Java application, a C or C++ application, or any other application or group of applications operating on a client device. In one embodiment, the user interface may be deployed through a Web browser. In one embodiment, the user interface may be deployed as an application running on a client device, with suitable software and/or hardware for access to an internetwork. In these and other embodiments, certain image processing functions may be distributed in any suitable manner between a client device and one or more servers, as will be explained in further detail below.

Figure 4:
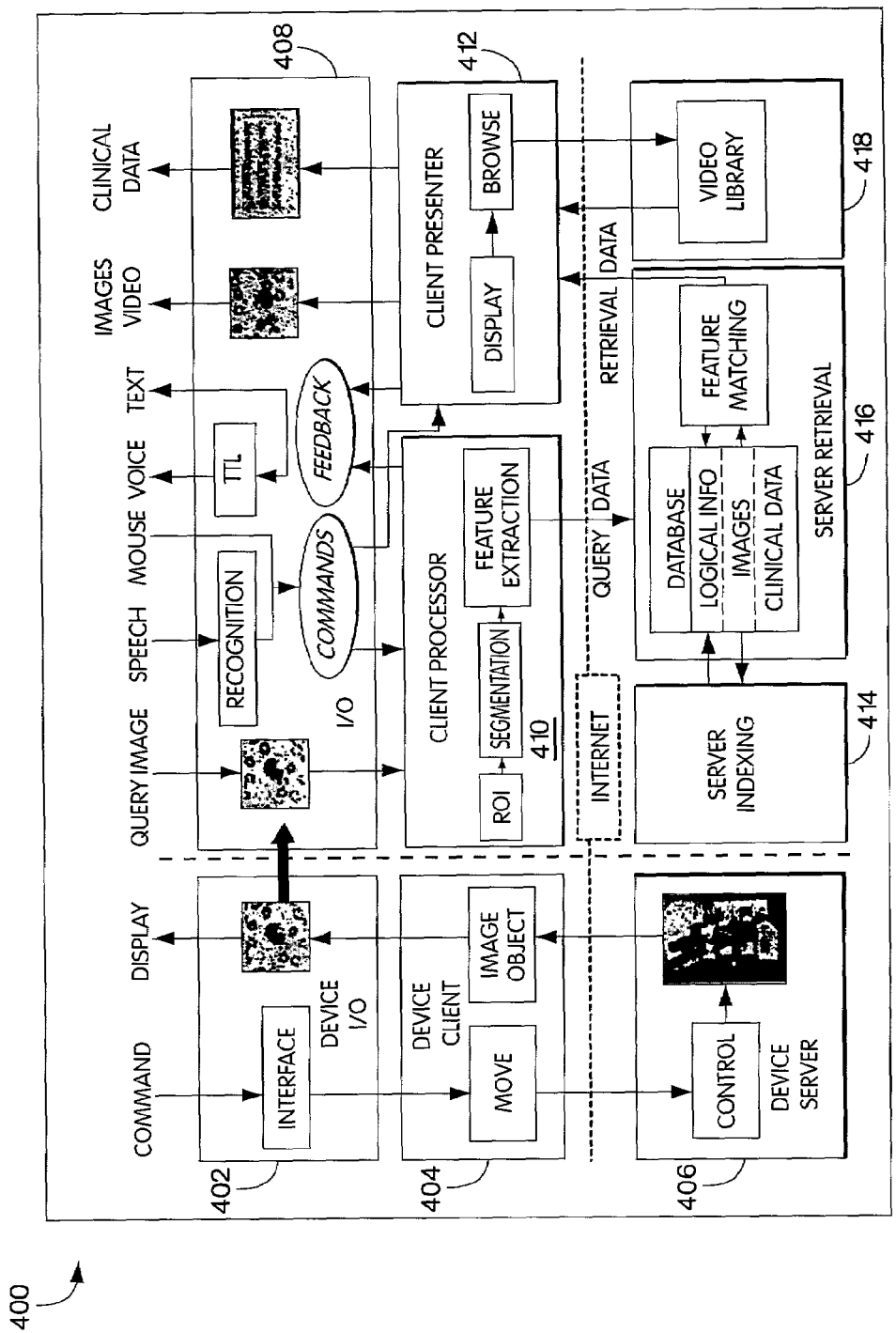
FIG. 4 shows a software architecture that may be used with a collaborative diagnostic system.

FIG. 4 shows a software architecture that may be used with a collaborative diagnostic system. Each component of the architecture 400 may be realized as computer executable code created using a structured programming language such as C, an object-oriented programming language such as C++ or Java, or any other high-level or low-level programming language that may be compiled or interpreted to run on one of the above devices, as well as heterogeneous combinations of processors, processor architectures, or combinations of different hardware and software. The architecture 400 may be deployed using software technologies or development environments including a mix of software languages, such as Microsoft IIS, Active Server Pages, Java, C++, Oracle databases, SQL, and so forth. Software modules within the architecture 400 may include a device input/output ("I/O") 402, a device client 404, a device server 406, a client input/output ("I/O") 408, a client processor 410, a client presenter 412, a server indexing 414, a server retrieval 416, and a video library 418.

The device I/O 402, the device client 404, and the device 406 may operate on a device, such as any of the devices described above, that is local to one of the imaging devices 101 of FIG. 1, or on the imaging device 101 where the imaging device 101 is programmable.

The device I/O 402 receives commands at one of the imaging devices 101. The commands may be input locally at a client 102 coupled to the imaging device 101, or may be received remotely from another client 102 connected to the internetwork 110. The commands are formatted for local use by the imaging device 101. The device I/O 402 also provides image output, from the imaging device 101 for local or remote use. The device client 404 receives commands from the device I/O 402 and presents them to the imaging device 101. The device client 404 also receives image data from the imaging device 101 and presents it to the device I/O 402.

In one embodiment, the device client 404 may autonomously direct scanning of an entire specimen, such as through step-wise x-axis and y-axis traversal, or any other systematic spatial traversal, of an entire specimen. An archival system within the device client 404 may provide unsupervised image feature extraction and automated management of images of additional biological specimens for addition to the database. During this process, the device client 404 may communicate with the imaging device 101 to autofocus (such as through entropy-based autofocusing) the device in each position. Further processing may include identification of areas of interest, such as cells within a specimen, along with increasing resolution of imaging within those areas of interest. In one embodiment, one or more specimens may be processed in this manner and stored in digital form in a database. The database may then be accessed in the same manner as an imaging device 101 for further use as described herein. This approach may be particularly advantageous where average access and use time for specimens under study is greater than the average processing time for a complete, autonomous image study performed by the device client 404, or where for other scheduling reasons it may be useful to free the imaging device 101 for other imaging tasks while the image data remains available for use with the systems described herein.

In an embodiment of the systems described herein, the device client 404 may also manage control of a software token that is provided for distributed control of the imaging device 101. It should be appreciated that a number of token management systems are possible, including, for example, centrally managed tokens or fully distributed token control. Such systems may provided for limited or unlimited duration of control by a token holder, and may include prioritized access to the token. All such token management schemes may be used with the systems described herein.

The device server 406 receives commands from the device client 404 and processes them for presentation to, and use by, the imaging device 101. For the Olympus AX70 imaging device noted above, this may include, for example, low-level realization of specimen stage, light level, objective lens selection, and focus functions. The device server 406 also controls image capture and digitization, along with presentation of captured images to the device client 404.

The client I/O 408, the client processor 410, and the client presenter 412 may operate on a client device 102 of FIG. 1, which may, as noted above be locally coupled to the imaging device 101 or remotely coupled to the imaging device 101 through the internetwork 110.

The client I/O 408 may receive a query image for investigation. The query image may be received from the imaging device 101, or from a database of image data. User input such as speech, mouse movements, and keyboard input may be received by the client I/O 408 and interpreted as commands for the system. Results may be processed for presentation to a user as voice data, text data, or image data. Image data from an image database may also be presented to a user through the client I/O 408, along with any clinical data associated with the image data.

The client processor 410 manages image processing functions, such as identification of regions of interest, segmentation of images and image data, and feature extraction of salient features from the image data for subsequent processing. Image processing is described in further detail below with reference to FIG. 5. The client processor 410 may also manage presentation of processed images to a remote server of diagnostic images as described below. The client presenter 412 may manage display and browsing of relevant diagnostic images retrieved from the remote server, under command of inputs received by the client I/O 408.

The server indexing 414, server retrieval 416, and video library 418 may operate on a server, such as one of the servers 104 of FIG. 1, which generally operates as a decision support system to provide image matching functions and access to image libraries and clinical data. The server indexing 414 provides an interface between one or more databases of image data and the search retrieval 416. The server retrieval 416 receives remote query data from a client 102, and generates a structured search of the database(s) managed by the server indexing 414. The server retrieval 416 performs feature matching and retrieves relevant images and clinical data from the server indexing 414, as described for example with reference to FIG. 5, below. Retrieval data may then be communicated over the internetwork 110 by the server indexing 414 of the server 104 to the client presenter 412 of the client 102. A video library 418 of image data and other data may also be maintained by the server 104 for direct access by the client presenter 412.

The server 104 may recognize several access levels, each having a different level of access to add, delete, and/or modify records stored by the server indexing 414. For example, a search group may have access to submit queries and to review local or remote images. An indexer group may have access to populate the image database with new images and associated diagnoses and clinical data. A reviewer group may have administrative access to add and remove authorized users from the system, control matching parameters described below with reference to FIG. 5, and review and modify existing entries in the database.

As will be described in more detail below, the architecture may be used to generate a query vector based upon an image under investigation, and submit the query vector to a search engine which will automatically identify and retrieve images, diagnoses, and correlated clinical data. The results, along with measures of similarity between a query vector and one or more confirmed diagnoses may then be presented to a user for further review. Having described a software architecture for use with a distributed system for computer-assisted discrimination of pathologies, a process for discrimination of pathologies that may be used within the software architecture will now be described in more detail.

Figure 5:
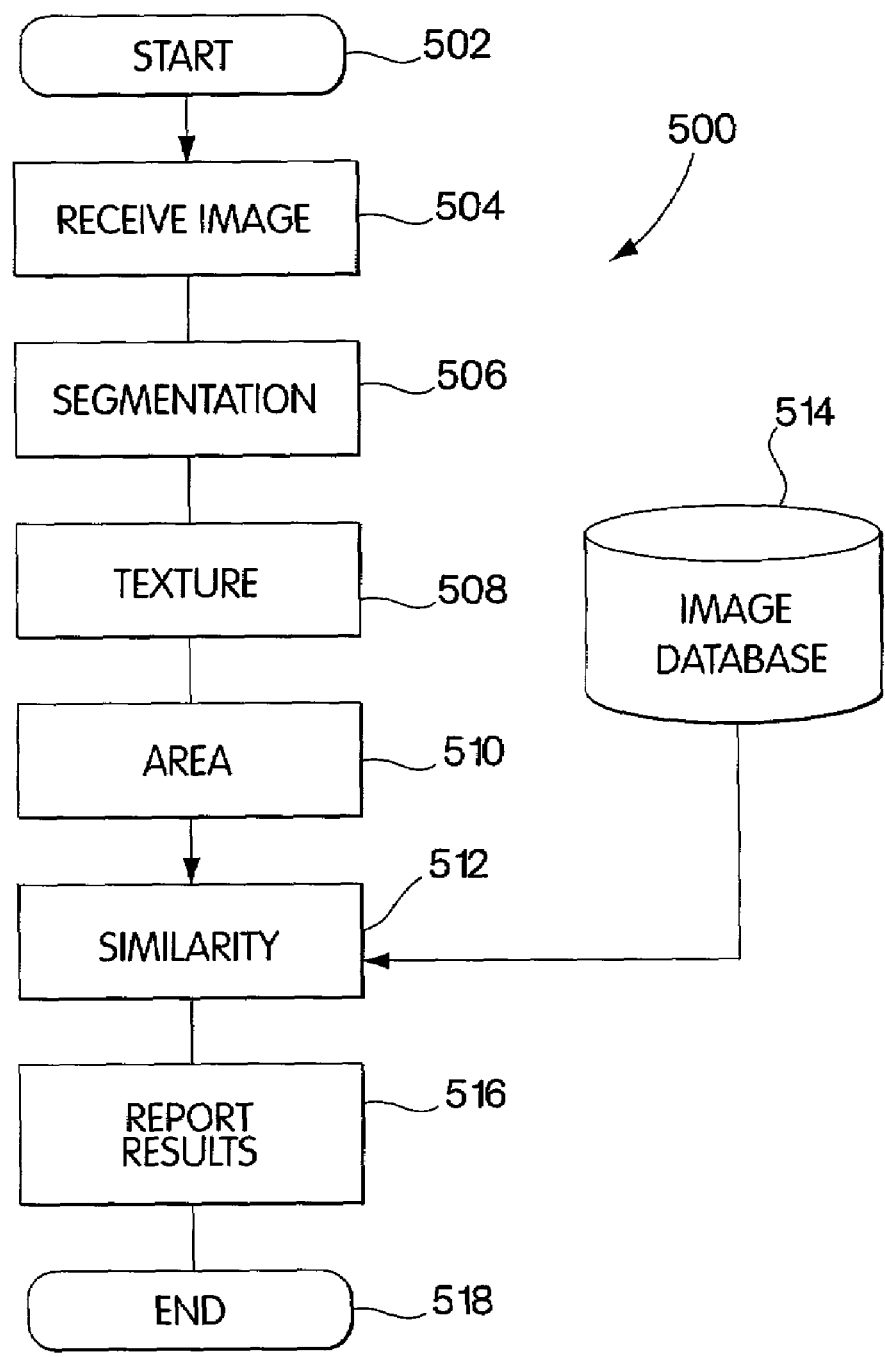
FIG. 5 is a flow chart of a process for computer-aided discrimination of pathologies.

FIG. 5 is a flow chart of a process for computer-aided discrimination of pathologies. The process 500 may be implemented to enable feature matching in the above software architecture. It will be appreciated that the below process 500 may be realized in hardware, software, or some combination of these. The process 500 may be realized in one or more microprocessors, microcontrollers, embedded microcontrollers, programmable digital signal processors or other programmable device, along with internal and/or external memory such as read-only memory, programmable read-only memory, electronically erasable programmable read-only memory, random access memory, dynamic random access memory, double data rate random access memory, Rambus direct random access memory, flash memory, or any other volatile or non-volatile memory for storing program instructions, program data, and program output or other intermediate or final results. The process 500 may also, or instead, include an application specific integrated circuit, a programmable gate array, programmable array logic, or any other device that may be configured to process electronic signals.

Any combination of the above circuits and components, whether packaged discretely, as a chip, as a chipset, or as a die, may be suitably adapted to use with the systems described herein. It will further be appreciated that the below process 500 may be realized as computer executable code created using a structured programming language such as C, an object-oriented programming language such as C++ or Java, or any other high-level or low-level programming language that may be compiled or interpreted to run on one of the above devices, as well as heterogeneous combinations of processors, processor architectures, or combinations of different hardware and software. The process 500 may be deployed using software technologies or development environments including a mix of software languages, such as Microsoft IIS, Active Server Pages, Java, C++, Oracle databases, SQL, and so forth.

The process 500 may start 502 when an image is received, as shown in step 504. The image may be, for example, a 24 bit TIFF format image of a specimen, such as a new, undiagnosed specimen that may potentially have a pathology, or an image in any other digital form, such as an image received from one of the imaging devices 101 of FIG. 1.

The image received in step 504 may be segmented, as shown in step 506. Segmentation may be accomplished by mapping red, green, and blue intensity values of the received TIFF image into L*u*v (luminance and chrominance) color space and utilizing a fast nonparametric clustering method. Once an outline of a shape has been identified, feature measurements may be characterized using, for example, elliptic Fourier descriptors. A closed curve, such as that describing a cell wall, or the boundaries of various cellular or anatomic components, or any other components of a biological specimen such as a cell, may be described with the following elliptical Fourier descriptors:

$$a_n = \frac{T}{2n^2\pi^2} \sum_{i=1}^{m} \frac{\Delta x_i}{\Delta t_i} \left[ \cos\left(\frac{2n\pi t_i}{T}\right) - \cos\left(\frac{2n\pi t_{i-1}}{T}\right) \right] \quad \text{[Eq's 1–4]}$$

$$b_n = \frac{T}{2n^2\pi^2} \sum_{i=1}^{m} \frac{\Delta x_i}{\Delta t_i} \left[ \sin\left(\frac{2n\pi t_i}{T}\right) - \sin\left(\frac{2n\pi t_{i-1}}{T}\right) \right]$$

$$c_n = \frac{T}{2n^2\pi^2} \sum_{i=1}^{m} \frac{\Delta y_i}{\Delta t_i} \left[ \cos\left(\frac{2n\pi t_i}{T}\right) - \cos\left(\frac{2n\pi t_{i-1}}{T}\right) \right]$$

$$d_n = \frac{T}{2n^2\pi^2} \sum_{i=1}^{m} \frac{\Delta y_i}{\Delta t_i} \left[ \sin\left(\frac{2n\pi t_i}{T}\right) - \sin\left(\frac{2n\pi t_{i-1}}{T}\right) \right]$$

where:

$$\Delta x_i = (x_i - x_{i-1}) \quad \text{[Eq's 5–9]}$$
$$\Delta y_i = (y_i - y_{i-1})$$
$$\Delta t_i = \sqrt{(\Delta x_i)^2 + (\Delta y_i)^2}$$
$$t_i = \sum_{j=1}^{i} \Delta t_i$$
$$T = \sum_{i=1}^{m} \Delta t_i$$

While a number of other techniques are available for image content-based indexing of object shapes, the above Fourier series advantageously preserve topology when truncated. For example, the above series may be usefully employed for discriminating among lymphoproliferative pathologies when truncated to ten harmonics (i.e., n=10), or forty coefficients.

As shown in step 508, a texture of the shape may be determined. Objective measurement of texture may be based upon, for example, a multiscale simultaneous autoregressive model (MRSAR), and more particularly, a second-order, noncausal model with five parameters at each resolution level. The algorithm may apply a symmetric MRSAR model to the luminance component of image data, with each luminance pixel value assumed to linearly depend upon neighboring pixel values. With an additive independent Gaussian noise term, a model may be stated as:

$$L^*(x) = \mu + \sum_{y \in \upsilon} \theta(y) L^*(y) + \varepsilon(x) \quad \text{[Eq. 10]}$$

where:

$L^*(x)$ is the pixel value at a location, x;

$\mu$ is the bias dependent on the mean value of $L^*$;

$\upsilon$ is the set of neighbors of the pixel at location x;

$\varepsilon(x)$ is additive Gaussian noise; and $\theta(y)$ and $y \in \upsilon$ are the model parameters.

The model parameters and the estimation error define a five-dimensional feature vector. In one embodiment, the MRSAR features may then be computed, for each location, for 5×5, 7×7, and 9×9 pixel neighborhoods to obtain a fifteen-dimensional multiresolution feature vector. More generally, features may be computed for variable-sized pixel neighborhoods and concatenated to generate a multi-dimensional, multi-resolution feature vector. Model parameters may then be estimated using overlapping windows, each offset by, for example, two pixels in the x-direction and the y-direction. Where 21×21 overlapping windows were used, the MRSAR features include a mean vector, t, and a covariance matrix across all 441 windows.

As shown in step 510, an area may be determined for each image. Where constant magnification of an imaging device is used, a direct calculation of area for the image may be obtained. Suitable scaling may be employed where image magnification varies from image to image.

As shown in step 512, a similarity comparison may be made between the image received in step 504, as processed into a 'query vector' or 'image profile', and one or more images in an image database 514. The image database may generally be any ground-truth database of images and diagnosed pathologies, each image having been processed as described above for the image received in step 504. The data in the image database 514 may be referred to as pathology profiles or pathology image profiles, which include processed data that is derived (e.g., as described above) from images having known pathologies. In one embodiment of a database of lymphoproliferative conditions, a ground-truth database of diagnoses for nineteen cases was independently confirmed by immunophenotyping. Subsequently, Wright stained peripheral blood smears were prepared for each specimen using standard methods of air drying, fixation with methanol, and staining with Wright Giemsa solution. Stained specimens were examined by a certified hematopathologist during the course of several sessions using a Leica microscope (40× planachromatic objective lens) while lymphoid cells and benign lymphocytes were identified, digitized and stored in 24-bit TIFF format. Other techniques are known for reliably diagnosing hematological conditions, including molecular studies and gene expression. These techniques may be similarly employed to prepare a ground-truth database for storage in the image database 514.

Generally, the image database 514 may include a pathology profile for one or more pathologies. This may include, for example a shape measure derived from a shape of one or more cells associated with the pathology, such as the shape vector using Fourier descriptors described above. This may also include a texture measure derived from a texture of the one or more cells associated with the pathology, such as the texture vector described above. This may also include an area measure derived from an area of the one or more cells associated with the pathology, or any other measure suitable for objective quantification. Each pathology profile may correspond to a particular instance of a diagnosed pathology, or each pathology profile may be formed of a composite, such as an average, of profiles for a number of different instances of the pathology. The image database 514 may also include other data, such as clinical data and any other data related to each image, that is not necessarily used for comparing images.

The query vector, or image profile, for an image received in step 504, for example, the vector of shape, texture, and area data for an image described above, or other multivariate vectors which may be used to characterize a pathology, may be compared to vectors for images stored in the image database using a weighted average of dissimilarity measures for each component. For a three parameter vector (although more or less than three may be used), this may be expressed as:

$$D = \sum_{i=1}^{3} w_i D_i \quad \text{[Eq's 11-12]}$$

$$\sum_{i=1}^{3} w_i = 1$$

where the distances used to determine similarity may be:

$$D_1 = \sqrt{(f_{query} - f_{ref})^T (f_{query} - f_{ref})}$$

$$D_2 = \sqrt{(t_{query} - t_{ref})^T \Sigma_{ref}^{-1} \cdot \sqrt{(t_{query} - t_{ref})}}$$

$$D_3 = \sqrt{(a_{query} - a_{ref})^T} \quad \text{[Eq's 13-15]}$$

A first distance measure, $D_1$, may be based upon image shape. In this case, a Euclidean distance may be calculated between vectors of Fourier coefficients for a reference and a query image, as shown above.

A second distance measure, $D_2$, may be based upon image texture. In this case, the distance is calculated as shown above, where $\Sigma^{-1}$ is the inverse of the covariance matrix for the reference image. The distance is a Mahalanobis distance between MRSAR feature vectors of the reference and the query image.

A third distance measure, $D_3$, may be based upon image area, as described more generally above. It will be appreciated that other distances may be used in conjunction with the distances described herein. For example, color may be used, provided that staining techniques, and other aspects of capturing images, are normalized for meaningful comparison.

In order to obtain weights to be used in the above calculations, each distance may be normalized to a standard deviation calculated relative to a center of the class, although it will be noted that the Mahalanobis distance used to quantify texture similarity is inherently normalized. The requirement that the weights, $w_1$, sum to one may be relaxed where the distances are not standardized to unit dimensions. Optimal weights may be determined using a number of different techniques. One useful technique is a downhill simplex method with an objective function, J, with optimization criterion based upon a retrieval matrix R defined as having an element $r_{jk}$ equal to the empirical probability of retrieval of class k images when the query belonged to class j. An objective function may be the trace of the retrieval matrix:

$$J = \text{trace } R = \sum_{j=1}^{m} r_{jj} \quad [\text{Eq. 16}]$$

In Eq. 16, m is the number of classes. An iterative search may be performed to find optimal weights. Starting from all weights equal, the objective function may be computed for the first eight retrievals (e.g., closest matches) over the entire database. The weights may then be modified and the procedure repeated until convergence is achieved.

In step 512, the predetermined weights developed as above, may be applied to obtain a weighted sum of distance measurements between a query vectors for a query image and reference vectors for a reference image. Results may then be reported in any suitable form, as shown in step 516. This may include display of quantitative similarity calculations, ranked by value, along with display of images having high (calculated) similarity. This may also include display of associated clinical data or other data which may assist in detecting, screening for, or discriminating among potential diagnoses. Computer-assisted decisions using the above visual similarity measurements have been demonstrated to improve accuracy of diagnosis for hematological malignancies when compared to unassisted visual inspection.

As shown in step 518, the process 500 may end. Optionally, the process 500 may return to step 504 where a new image is received for analysis. Having described a process for comparing images, a user interface for reviewing results of the comparison is now described in further detail.

Figure 6:
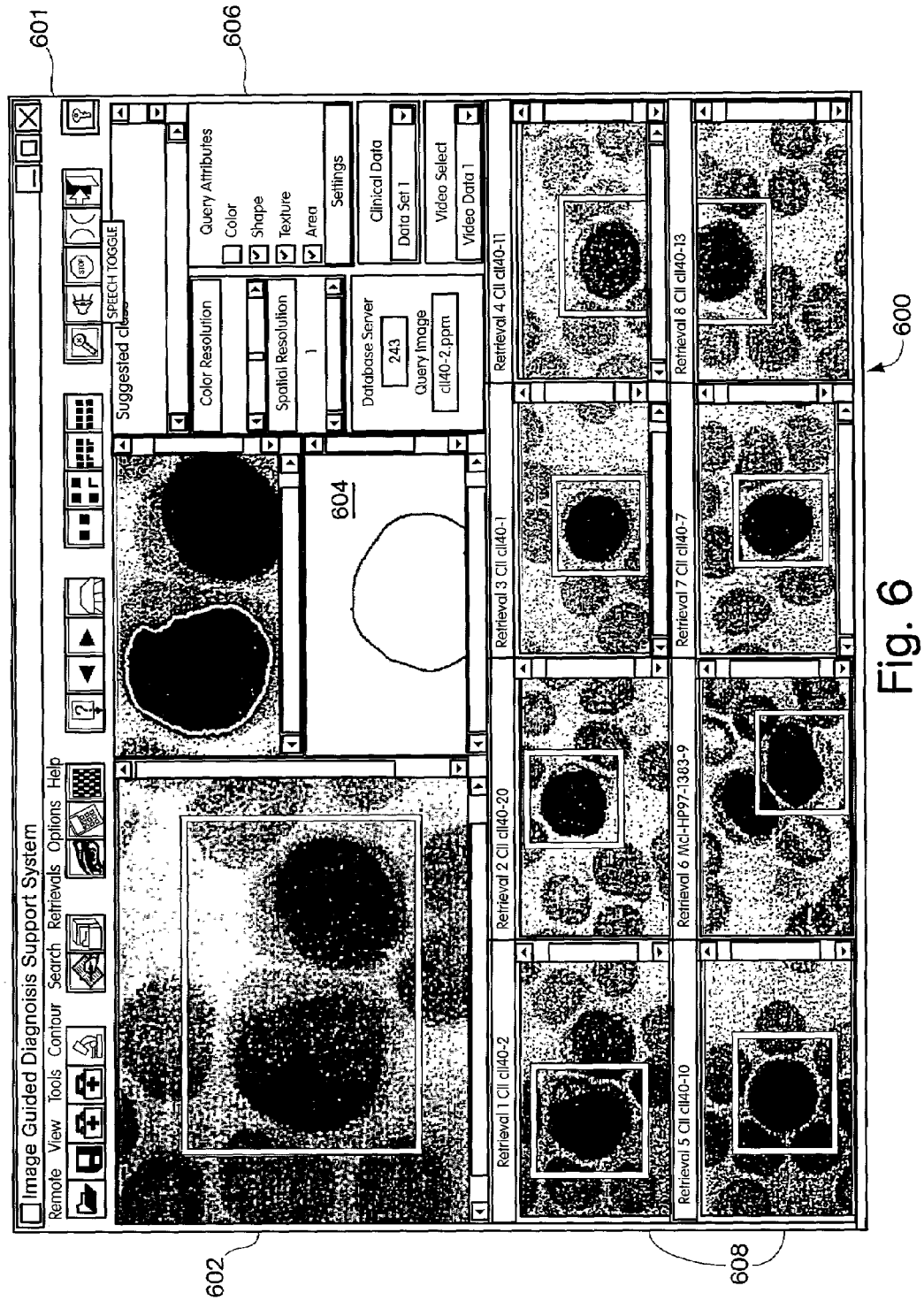
FIG. 6 is a user interface that may be used with a collaborative diagnostic system.

FIG. 6 is a user interface that may be used with a collaborative diagnostic system. The user interface 600 may include a toolbar 601, a current image workspace 602, a processed image workspace 604, a processing control workspace 606, and one or more matched image workspaces 608.

The toolbar 601 may include user controls for navigating within the system described above, including token control, imaging device control, selection of images for review, and other tools for initiating analysis, controlling analysis parameters, saving images, and so forth.

The current image workspace 602 may display an image currently under investigation. A user may, through the current image workspace 602, navigate through an entire image or, for example, identify a region of interest within an image. A user may also navigate through data sets of a plurality of images available to the system. The processed image workspace 604 and the processing control workspace 606 may permit control over image processing and search parameters. For example, a contour corresponding to a number of elliptical Fourier coefficients for a selected object may be displayed, and a user may visually determine whether more or less coefficients may be appropriate for adequately characterizing an image. One or more query attributes (e.g., color, shape, texture, area, etc.) may be specified for quantitative similarity calculations. Databases, clinical data, video sources, and so forth may be specified, as well as image parameters such as spatial resolution or color resolution for either display or computer-assisted analysis.

The one or more matched image workspaces 608 may display image data for images retrieved from an image database based upon quantitative comparison to the query image. Matched images may be displayed in order of similarity, or classified by pathology, or according to some other hierarchical scheme. Clinical data for matched images may also be displayed, including a confirmed diagnosis for each image.

It will be appreciated that the above functionality is merely illustrative, and that other interfaces and interface tools may be usefully deployed with a computer-assisted diagnosis system as described herein. For example, a messaging service may be included for communicating through electronic mail, instant messaging, other text-based services, audio, and so forth, between clinicians viewing a common query image and search results at remote locations. The system may generate a suggested or probable diagnosis based upon quantitative similarity between a query image and one or more reference images. These and other functions may be incorporated into the interface 600 of FIG. 6. Further, tools and controls for administrative functions such as adding, deleting, or modifying access for various users, or for submitting reference images, may be included in the interface 600 of FIG. 6, or in another interface configured for administrative functions.

It will be appreciated that many combinations of the above elements may be used with the systems described herein. All such combinations are intended to fall within the scope of the invention described herein. Thus, while the invention has been disclosed in connection with the preferred embodiments shown and described in detail, various modifications and improvements thereon will become readily apparent to those skilled in the art. It should be understood that all matter contained in the above description or shown in the accompanying drawings shall be interpreted as illustrative, and not in a limiting sense, and that the following claims should be interpreted in the broadest sense allowable by law.

What is claimed is:

1. A system comprising:
    a microscope that provides an image of a biological specimen in digital form, the microscope responsive to a control signal to change a parameter used to obtain the image of the biological specimen, the parameter including at least one of an objective lens, a focus, a light level, and a specimen position;
    a database that includes one or more pathology profiles associated with one or more pathologies, the one or more pathology profiles derived from images of one or more other biological specimens having one or more pathologies;
    a decision support system that processes the image from the microscope to obtain an image profile, the image profile including descriptive data of the image, the decision support system comparing the image profile to the one or more pathology profiles in the database to identify one or more of the one or more pathologies that are candidates for a pathology associated with the biological specimen; and
    a client interface through which one or more remote users receive the image of the biological specimen and provide input to the system including at least one of generating the control signal to the microscope, communicating with other ones of the one or more remote users, and controlling operation of the decision support system.

2. The system of claim 1 wherein the microscope employs an auto-focusing algorithm that retains a history of one or more previous auto-focus settings.

3. The system of claim 1 further comprising an archival system which provides unsupervised image feature extraction and automated management of images of additional biological specimens for addition to the database.

4. The system of claim 1 wherein the decision support system is trained using a ground truth database of images having independently confirmed pathologies.

5. The system of claim 4 wherein the pathologies are independently confirmed using at least one of immunophenotyping, molecular studies, or gene expression.

6. The system of claim 1 wherein the decision support system compares the image profile to one of the one or more pathology profiles by quantitatively comparing a derived measure of shape, texture, and area for the image profile to a derived measure of shape, texture, and area for the one of the one or more pathology profiles.

7. The system of claim 6 wherein the derived measure of shape comprises a plurality of elliptical Fourier coefficients for an outline of a shape of one or more components of the biological specimen.

8. The system of claim 6 wherein the derived measure of texture is calculated using a multiscale simultaneous autoregressive model.

9. The system of claim 1 wherein the one or more pathologies include hematological disorders.

10. A method comprising:
providing a database that includes one or more pathology profiles associated with one or more cells having one or more pathologies, the pathology profile for each pathology including a shape measure derived from a shape of one or more cells associated with the pathology, a texture measure derived from a texture of the one or more cells associated with the pathology, and an area measure derived from an area of the one or more cells associated with the pathology;
receiving an image of a cell in digital form;
processing the received image to obtain a query vector that includes a shape measure of the cell in the received image, a texture measure of the cell in the received image, and an area of the cell in the received image; and
comparing the query vector to the one or more pathology profiles in the database to obtain a quantitative measure of similarity between the cell in the received image and one of the one or more cells having one or more pathologies.

11. The method of claim 10 further comprising suggesting a diagnosis for the cell in the received image based upon the quantitative measure of similarity.

12. The method of claim 10 wherein comparing the query vector to the one or more pathology profiles further comprises calculating, for each pathology profile in the database, a weighted sum of a difference between each of the shape measure, the texture measure, and the area for the pathology profile and the shape measure, the texture measure, and the area for the query vector.

13. The method of claim 10 wherein the one or more pathologies include one or more hematological disorders.

14. The method of claim 10 wherein processing the received image to obtain a query vector that includes a shape measure of the cell in the received image further comprises:
converting the image from a red-green-blue representation to a luminance-chrominance representation;
locating a plurality of coordinates of an outer boundary of at least one of the cell or one or more constituent components of the cell; and
characterizing the outer boundary with a plurality of elliptical Fourier coefficients.

15. The method of claim 10 wherein processing the received image to obtain a query vector that includes a texture measure of the cell in the received image further comprises selecting a plurality of overlapping windows within the received image and, for each one of the plurality of overlapping windows, calculating a texture at a plurality of resolutions.

16. The method of claim 15 further comprising applying a multiscale simultaneous autoregressive model.

17. A system comprising:
database means for providing a database that includes one or more pathology profiles associated with one or more cells having one or more pathologies, the pathology profile for each pathology including a shape measure derived from a shape of one or more cells associated with the pathology, a texture measure derived from a texture of the one or more cells associated with the pathology, and an area measure derived from an area of the one or more cells associated with the pathology;
imaging means for receiving an image of a cell in digital form;
processing means for processing the received image to obtain a query vector that includes a shape measure of the cell in the received image, a texture measure of the cell in the received image, and an area of the cell in the received image; and
comparing means for comparing the query vector to the one or more pathology profiles in the database to obtain a quantitative measure of similarity between the cell in the received image and one of the one or more cells having one or more pathologies.

18. A computer read medium having machine executable instructions for causing a data processing apparatus to perform a method comprising:
providing a database that includes one or more pathology profiles associated with one or more cells having one or more pathologies, the pathology profile for each pathology including a shape measure derived from a shape of one or more cells associated with the pathology, a texture measure derived from a texture of the one or more cells associated with the pathology, and an area measure derived from an area of the one or more cells associated with the pathology;
receiving an image of a cell in digital form;
processing the received image to obtain a query vector that includes a shape measure of the cell in the received image, a texture measure of the cell in the received image, and an area of the cell in the received image; and
comparing the query vector to the one or more pathology profiles in the database to obtain a quantitative measure of similarity between the cell in the received image and one of the one or more cells having one or more pathologies.

19. A method of doing business comprising:
providing a database that includes one or more pathology profiles associated with one or more pathologies, the pathology profile for each pathology including a shape, a texture, and an area for one or more images of biological specimens that carry the pathology;

providing a decision support system for comparing a new specimen to the one or more pathology profiles and identifying a pathology from the one or more pathology profiles associated with the new specimen; and providing a server that includes a client interface through which a user may submit the new specimen to the decision support system from a remote location in a network, the server providing a result from the decision support system to the user at the remote location.

20. The method of claim 19, the server further configured to share the result and the image among a plurality of users, and to forward electronic communications between two or more of the plurality of users.

21. The method of claim 20 wherein the electronic communications include at least one of instant messaging, audio, text, or electronic mail.

22. The method of claim 19 further comprising:

providing a microscope that provides an image of a biological specimen in digital form, the microscope responsive to a control signal to change a parameter used to obtain the image of the biological specimen, the parameter including at least one of an objective lens, a focus, a light level, and a specimen position; and providing a user interface through which one or more of a plurality of users, connected to the client interface through a data network, receive the image of the biological specimen and generate the control signal to the microscope.

23. The method of claim 22 wherein one of the plurality of users has a token that provides to the one of the plurality of users exclusive control over the control signal to the microscope.

24. The method of claim 19 wherein the decision support system compares a measure of shape, a measure of texture, and an area of the new specimen to a measure to a measure of shape, a measure of texture, and an area of each of the one or more pathology profiles.

* * * * *